(12) United States Patent
Lynn

(10) Patent No.: US 8,747,737 B2
(45) Date of Patent: Jun. 10, 2014

(54) AIR DECONTAMINATION UNIT

(75) Inventor: Daniel W. Lynn, Omaha, NE (US)

(73) Assignee: Food Safety Technology, LLC, Omaha, NE (US)

( * ) Notice: Subject to any disclaimer, the term of this patent is extended or adjusted under 35 U.S.C. 154(b) by 492 days.

(21) Appl. No.: 13/054,291

(22) PCT Filed: Jul. 10, 2009

(86) PCT No.: PCT/US2009/050235
§ 371 (c)(1),
(2), (4) Date: Mar. 25, 2011

(87) PCT Pub. No.: WO2010/009012
PCT Pub. Date: Jan. 21, 2010

(65) Prior Publication Data
US 2011/0165018 A1    Jul. 7, 2011

Related U.S. Application Data

(60) Provisional application No. 61/080,488, filed on Jul. 14, 2008.

(51) Int. Cl.
| | | |
|---|---|---|
| *A61L 9/00* | (2006.01) | |
| *A61L 2/00* | (2006.01) | |
| *A62B 7/08* | (2006.01) | |
| *G01N 23/00* | (2006.01) | |
| *B01D 46/00* | (2006.01) | |
| *A61K 8/22* | (2006.01) | |
| *A61L 2/18* | (2006.01) | |
| *A61L 2/20* | (2006.01) | |
| *A61L 9/015* | (2006.01) | |
| *A61L 9/03* | (2006.01) | |
| *A61L 9/20* | (2006.01) | |
| *A01N 1/02* | (2006.01) | |

(52) U.S. Cl.
CPC .................. *A61K 8/22* (2013.01); *A61L 2/0017* (2013.01); *A61L 2/183* (2013.01); *A61L 2/202* (2013.01); *A61L 9/00* (2013.01); *A61L 9/015* (2013.01); *A61L 9/032* (2013.01); *A61L 9/20* (2013.01); *A01N 1/0294* (2013.01)
USPC .................. 422/24; 422/124; 95/273; 96/224; 250/455.11; 250/492

(58) Field of Classification Search
CPC ........ A61K 8/22; A61L 2/0017; A61L 2/183; A61L 2/202; A61L 9/015; A61L 9/032; A61L 9/20; A01N 1/0294; C01B 13/11
USPC ............. 422/4, 24, 121–124; 95/273; 96/224; 250/455.11, 492
See application file for complete search history.

(56) References Cited

U.S. PATENT DOCUMENTS

| | | |
|---|---|---|
| 5,536,400 A | 7/1996 | Schultz |
| 5,601,786 A | 2/1997 | Monagan |

(Continued)

OTHER PUBLICATIONS

International Search Report for International Publication No. WO2010/009012A1 (PCT/US2009/050235) dated Sep. 1, 2009 (3 pages).

*Primary Examiner* — Monzer R Chorbaji
(74) *Attorney, Agent, or Firm* — Polsinelli PC

(57) ABSTRACT

An air decontamination unit is described with a housing defining an interior, an intake and exhaust in direct communication with the interior, a blower—in operational communication with a control panel—for drawing in and moving air through the housing, which further includes a filter assembly, a UV lamp, an ozone lamp, and an ozone sensor for detecting the concentration of ozone therein—positioned in the interior of the housing, all in direct communication with the control panel.

23 Claims, 6 Drawing Sheets

(56) References Cited

U.S. PATENT DOCUMENTS

| | | |
|---|---|---|
| 5,833,740 A | 11/1998 | Brais |
| 6,589,486 B1 | 7/2003 | Spanton |
| 6,589,489 B2 | 7/2003 | Morrow et al. |
| 6,613,277 B1 | 9/2003 | Monagan |
| 6,809,326 B2 | 10/2004 | Disabito et al. |
| 6,824,693 B1 | 11/2004 | Sauska et al. |
| 6,939,397 B2 | 9/2005 | Nelsen et al. |
| 7,081,225 B1 | 7/2006 | Hollander |
| 7,300,499 B1 | 11/2007 | Fleisher |
| 7,326,387 B2 * | 2/2008 | Arts et al. ............ 422/186.3 |
| 2004/0265193 A1 | 12/2004 | Panice et al. |
| 2005/0175498 A1 | 8/2005 | Nelson |
| 2005/0186108 A1 | 8/2005 | Fields |
| 2005/0226762 A1 | 10/2005 | Naarup |
| 2006/0153749 A1 | 7/2006 | Schroder |
| 2007/0041882 A1 | 2/2007 | Rosenberry et al. |
| 2007/0101867 A1 | 5/2007 | Hunter et al. |
| 2007/0119699 A1 | 5/2007 | Chambers et al. |
| 2007/0181000 A1 | 8/2007 | Wilson et al. |
| 2007/0253860 A1 | 11/2007 | Schroder |

\* cited by examiner

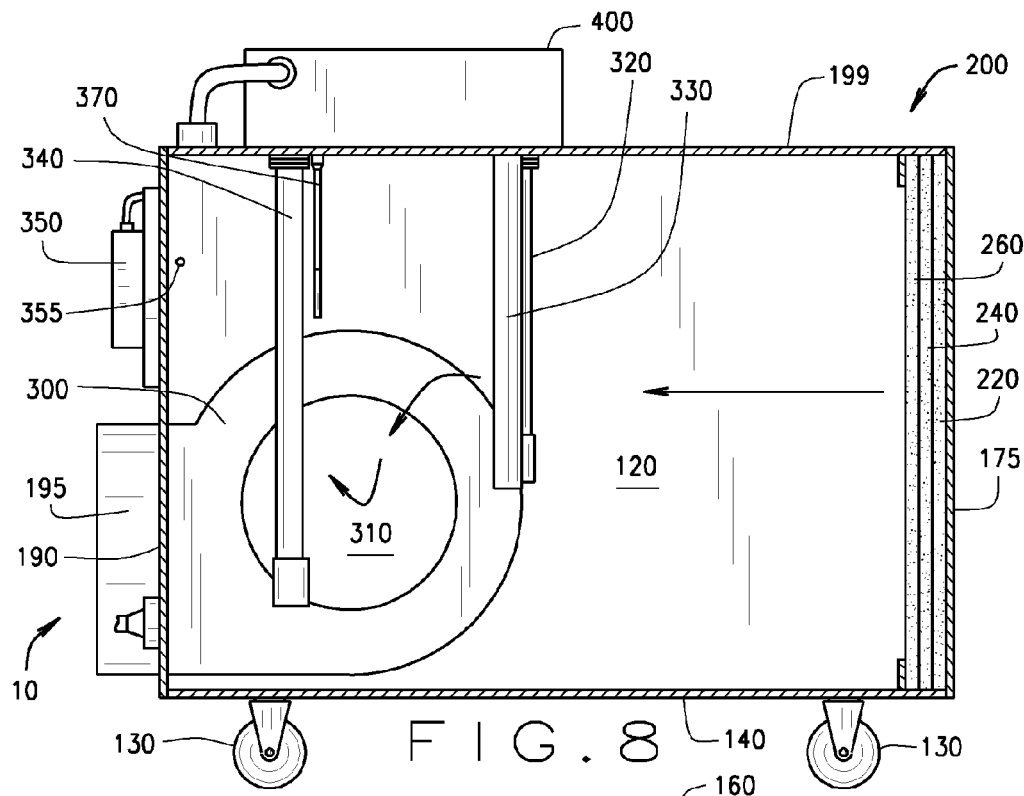
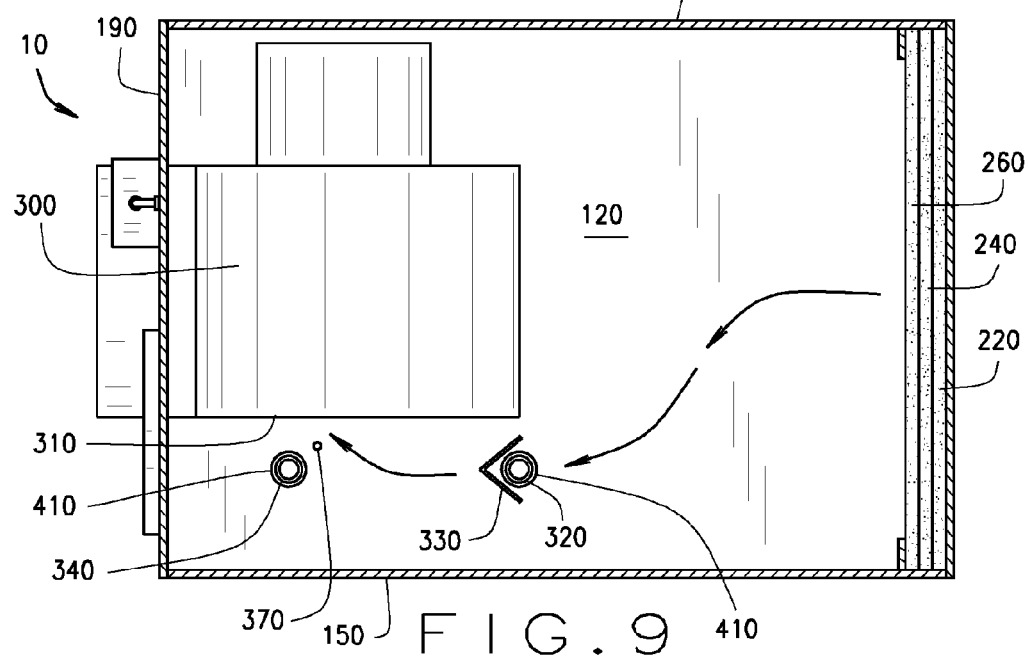

AIR DECONTAMINATION UNIT

FIELD OF INVENTION

The present invention relates to an air decontamination unit that uses a filter assembly, ozone gas, and ultraviolet light to clean and sanitize air.

BACKGROUND OF INVENTION

Previous attempts in decontaminating air have involved filtering. Unfortunately, filtering does not eliminate pathogens or destroy microorganisms present in the air. Other attempts in providing systems for decontaminating air have involved the use of ultraviolet light and/or ozone production in bulky systems or systems requiring permanent fixation into the existing HVAC structure. These systems are generally confined to a single location or require modification of existing HVAC structures. Other attempts in providing systems for decontaminating air have provided ultraviolet light and/or ozone production, but have failed to utilize the ultraviolet light or ozone in a system that generates a high velocity of air, which cleans and sanitizes a room.

SUMMARY OF INVENTION

An air decontamination unit is described that utilizes a filter assembly, ozone gas and ultraviolet light to clean and sanitize air. The air decontamination unit provides a high velocity of cleaned and sanitized air into its ambient environment. The air decontamination unit is portable and may be easily moved from one location to another location. The air decontamination may be provided with wheels and handles to aid in the transport between locations.

The air decontamination unit comprises a housing defining an interior. The housing further comprises an intake and an exhaust, wherein the intake and exhaust are in communication with the interior of the air decontamination unit. Air enters the housing via the intake, and after the air is cleaned and sanitized, the air exits the housing via the exhaust. A blower is positioned relative to the interior for drawing air into the housing and moving air through the interior of the housing. The housing further comprises a filter assembly for filtering the air entering the housing through the intake. A control panel is in operational communication with the blower. An ozone lamp is positioned in the interior of the housing. The ozone lamp is in electrical communication with the control panel. A UV lamp is positioned in the interior of the housing. The UV lamp is in electrical communication with the control panel. An ozone sensor is in electrical communication with the control panel for measuring the concentration of ozone gas in the interior of the housing.

The cleaned and sanitized air is exhausted from the housing of the unit at a high volume and velocity sufficient to remove and/or destroy a substantial amount of the microorganisms and pathogens present in the operating environment of the unit. The high velocity of the exhaust air circulates about the room and expands into cracks and crevices where microorganisms, pathogens and contaminants may be located. The unit processes high volumes of air at a high velocity, up to approximately 3000 cubic feet per minute, to process the air in the room.

DESCRIPTION OF FIGURES

FIG. 8 is a side, sectional view the air decontamination unit.
FIG. 9 is top, sectional view of the air decontamination unit.

DETAILED DESCRIPTION OF INVENTION

Figure 1:
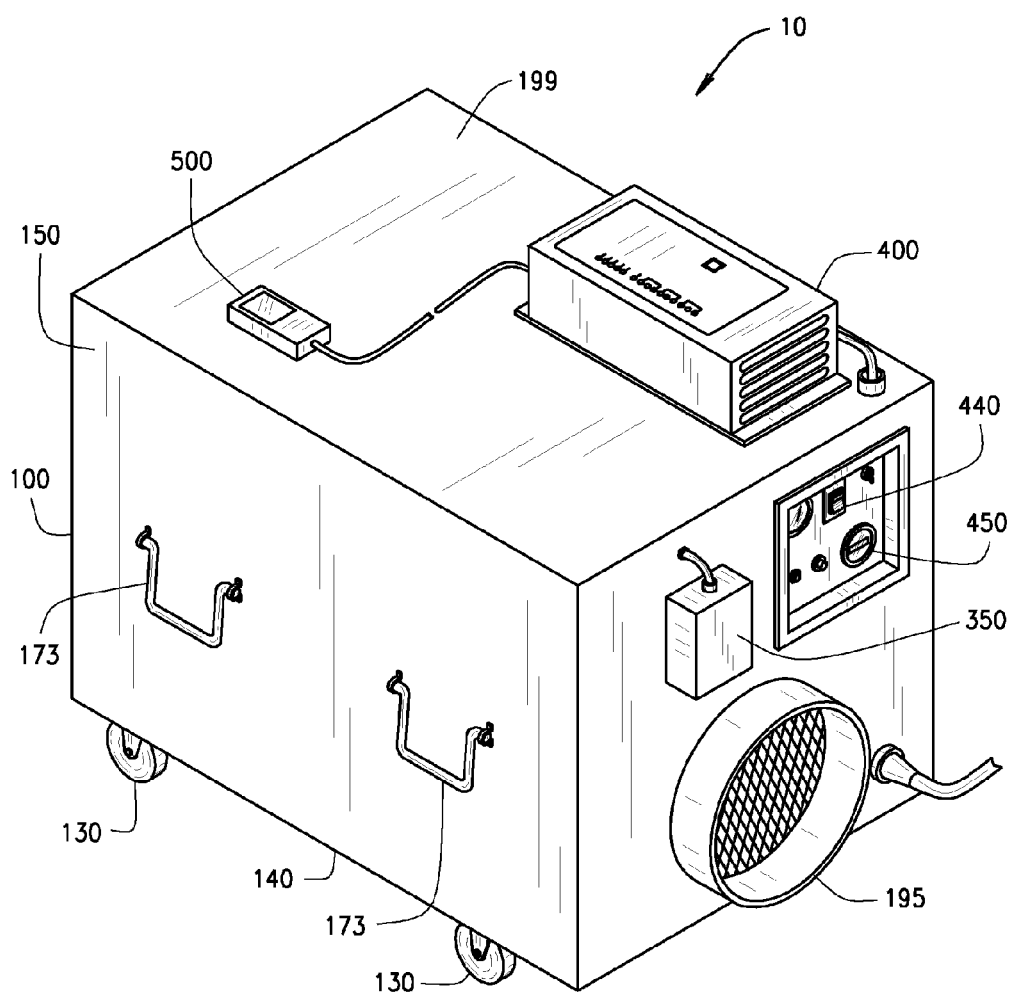
FIG. 1 is a perspective view of the air decontamination unit.

An air decontamination unit is described herein. The air decontamination unit provides a high velocity of cleaned and sanitized air into its ambient environment. The negative pressure created by the air decontamination unit intensifies the cleaning and sanitizing processes of the air decontamination unit. The air decontamination unit provides germicidal killing power of approximately 200 to 8000 microwatts and a 0-100% variable ozone output. The air decontamination unit eliminates microorganisms, bacteria and viruses from ambient air along with odor from smoke, pet and food preparation.

The air decontamination unit may be safely and effectively utilized in nearly any type of facility. The air decontamination unit is suitable for restaurants, bars, senior care living facilities, commercial office buildings, veterinary clinics, schools, child care facilities, hospitals and the like. Use of the air decontamination unit in such facilities will reduce pathogens in the ambient air, reduce infection, and reduce the incidence of sickness caused by airborne pathogens. The air decontamination unit may be utilized in meat lockers and storage facilities and produce/vegetable storage facilities to improve and extend the shelf-life of food items. The air in meat processing facilities is prone to picking up proteins of the hide and carcasses. These proteins encourage growth of microorganisms, which lead to food spoilage. By destroying the microorganisms, the decay of the food items is reduced, and the shelf-life of the food items is increased creating value for the food industry.

The air decontamination unit provides germicidal and odor protection through a centralized system comprising filters, a UV lamp, and an ozone lamp. The ultraviolet lamp emits radiation that directly destroys microorganisms. The ozone lamp emits radiation that forms ozone gas that cleans and sanitizes the air. The air decontamination unit includes one or more filters to remove particulates and pathogens from the air. A control system monitors and operates the air decontamination unit. The air decontamination unit may operate as a stand-alone device. The air decontamination unit may also be incorporated into the infrastructure of an existing HVAC system. The air decontamination unit may also operate with a number of similar air decontamination units in a room or facility.

The air decontamination unit eliminates pathogens and microorganisms from the ambient air in the room or facility in which the operating air decontamination unit is located. Bacteria, fungus, mold spores, viruses, yeasts, cysts, algae, fungal pathogens, and protozoa are all eliminated by the operation of the air decontamination unit.

With reference to FIGS. 1-9, an air decontamination unit 10 is shown. The air decontamination unit 10 is portable and may be easily rolled from one room requiring air decontamination to a second or additional rooms also requiring air decontamination.

The air decontamination unit 10 comprises a housing 100, which forms a box-like structure. The housing 100 may be made from aluminum or other sturdy and non-reactive material. As shown in FIGS. 8 and 9, the housing includes an interior 120, which aids in directing the air flow through the air decontamination unit 10. Ambient air is drawn into the air decontamination unit 10 and the air is cleaned and sanitized. The cleaned and sanitized air is exhausted from the air decontamination unit 10 into a room or facility. The cleaned and sanitized air is safe for direct contact with the occupants of the room or facility.

The housing 100 includes wheels 130 for mobility. As shown in FIG. 1, the air decontamination unit comprises four wheels 130 engaged with a bottom surface 140 of the air decontamination unit 10. The wheels 130 may be replaced with casters, tracks, slides, etc. that also provide for mobility for the air decontamination unit 10.

Figure 2:
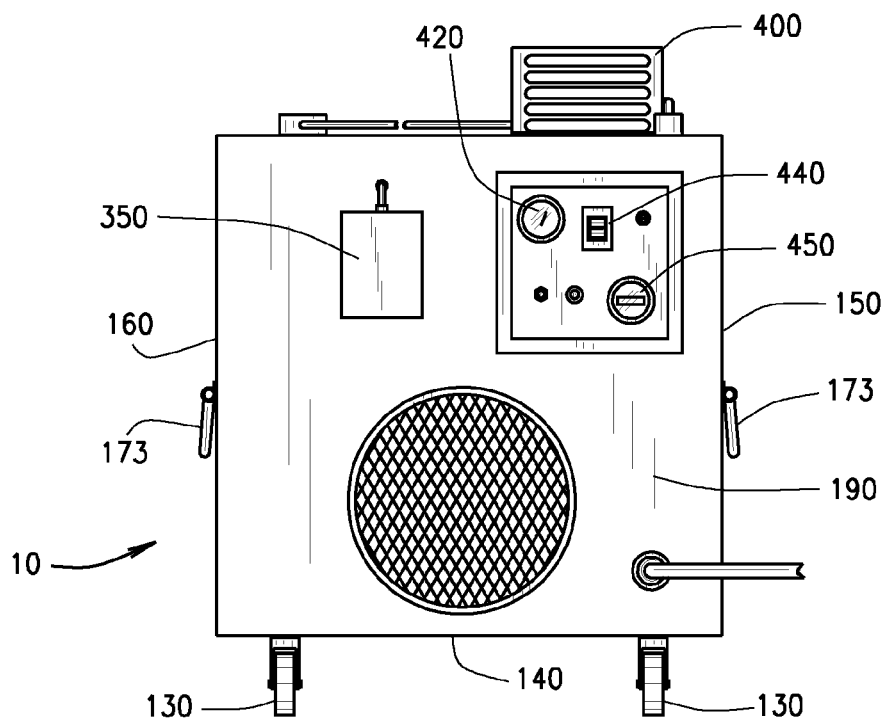
FIG. 2 is a view of the exhaust side of the air decontamination unit.
Figure 3:
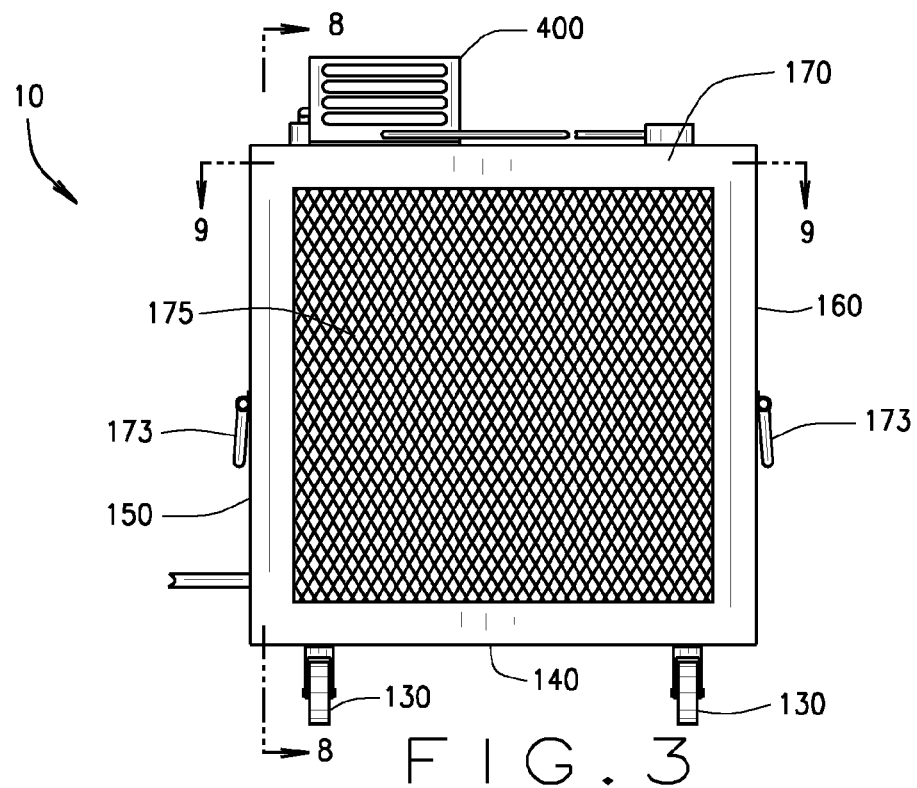
FIG. 3 is view of the intake side of the air decontamination unit.

Exterior sides 150 and 160 of the air decontamination unit 10 comprise four handles 173 to allow the operator to hold and maneuver the air decontamination unit 10 during transport from a first room to a second room. As shown in FIG. 3, an intake side 170 of the air decontamination unit 10 comprises an intake manifold 175. As shown in FIG. 2, an exhaust side 190 of the housing 100 is opposite of the intake side 170. The exhaust side 190 comprises an exhaust port 195.

As shown in FIGS. 8 and 9, a filter assembly 200 is positioned on the intake side 170 of the housing 100. The filter assembly 200 filters the incoming ambient air entering the housing 100 from the intake side 170. The filter assembly 200 removes particles, bacteria and other contaminants from the air entering the air decontamination unit 10 from the intake manifold 175. The filter assembly 200 comprises one or more particulate filters 220, an anti-bacterial filter 240, and a 0.3 micron hepa filter 260. The particulate filter 220, anti-bacterial filter 240, and the 0.3 micron hepa filter 260 are commercially available and may have an industry standard sizes of 24 inches by 24 inches. The particulate filter 220 removes particles up to 10 microns and larger from air entering the unit 10. The anti-bacterial filter 240 removes particles up to 1 micron and larger from the air entering the unit 10. The filter assembly 200 remove particulate from the air entering the housing 100.

A blower 300 draws air into the interior 120 of the housing 100 through the intake manifold 175 and the filter assembly 200. After passing through the interior 120 of the housing 100 and the filter assembly 200 for processing, the blower 300 exhausts the air through the exhaust port 195 of the housing 100. Before the air is exhausted via the exhaust port 195, the air passes first through the filter assembly 200 for filtration. Next, the air contacts a UV lamp 320 such that the UV radiation from the UV lamp 320 destroys microorganism present in the air. Finally, the air is subjected to and mixed with ozone gas created by an ozone lamp 340. The arrangement of filter assembly 200, the UV lamp 320 and the ozone lamp 340 with and in the housing 100 provide for the incoming air to first be filtered, followed by exposure to UV light, and then mixed and contacted with the ozone gas.

A suitable UV lamp 320 is a hot filament lamp. The UV lamp 320 emits radiation at a wavelength of approximately 248 nanometers to approximately 260 nanometers. The UV lamp 320 has an output of approximately 200 microwatts to approximately 8000 microwatts. In the embodiment shown, the UV lamp 320 is commercially available from Light-Sources, Inc. and LightTech Lamp Technology Ltd. and is made from quartz glass. This particular UV lamp 320 emits radiation at 254 nanometers, which kills germs present in the air. The UV lamp 320 is rated for a life of approximately 20,000 hours.

A UV lamp trap 330 partially surrounds the UV lamp 320. The UV lamp trap 330 acts as a deflector or shield to increase the contact time of the ambient air with the radiation emitted by the UV lamp 320. The UV lamp trap 330 may comprise an angled, a rounded, or semi-circular plate or extension extending most of or the entire length of the UV lamp 320. The UV lamp trap 320 provides a physical barrier that slows or temporality traps air adjacent to the UV lamp trap 320 for UV treatment. The UV lamp trap 330 is on the side of the UV lamp 320 opposite of the incoming air flow through the filter assembly 200.

After the air passes the UV lamp 320 and the UV lamp trap 330, the air next passes the ozone lamp 340. The ozone lamp 340 is a hot filament lamp with a quartz tube that emits radiation that creates ozone gas from the oxygen molecules found in the ambient air entering the air decontamination unit 10. The ozone lamp 340 emits radiation at a wavelength of approximately 180 nanometers to approximately 190 nanometers. In the embodiment shown, the ozone lamp 340 is commercially available from LightSources, Inc. and LightTech Lamp Technology Ltd. and emits radiation at 185 nanometers. The ozone lamp 340 provides instant-start for ozone production and operates at 25 watts. The ozone lamp 340 is rated for a life of approximately 20,000 hours. The ozone output of the ozone lamp 340 is adjustable to provide varying levels of ozone.

The ozone gas formed by the ozone lamp 340 cleans and sanitizes the ambient air. The ozone gas also mixes with air. After passing the ozone lamp 340, the air is drawn into an entry side 310 of the blower 300 and the blower 300 forces the now-cleaned and sanitized air comprising ozone gas through the exhaust port 195 and into the room containing the air decontamination unit 10. The exhausted air contains a concentration of ozone gas at approximately or just under 0.1 ppm to sanitize and clean the ambient air in a room.

An ozone sensor 350 measures the concentration of ozone in the air exhausted by the air decontamination unit 10. The ozone sensor 350 comprises a probe 355 that is positioned on an interior side of the exhaust side wall 190. The ozone sensor 350 is in electrical communication with the control panel 400. When an ozone concentration of greater than 0.1 ppm is measured by the ozone sensor 350 and this measurement is relayed to the control panel 400, the control panel 400 shuts off the ozone lamp 340. After the ozone level has lowered to a lower threshold level of approximately 0.09 ppm, as measured by the ozone sensor 350, the control panel 400 turns the ozone lamp 340 back on to again create ozone gas within the air decontamination unit 10. As such, the control panel 440 monitors and operates the ozone lamp 340 to maintain a constant ozone residue at approaching or approximately just under 0.1 ppm. This feature prevents the air decontamination unit 10 from increasing the ozone levels in the exhaust air above workplace safety standards set by OSHA. In other embodiments, the lower threshold to turn the ozone lamp 340 back on is approximately 0.07 ppm to approximately 0.08 ppm. In other embodiments, the lower threshold may be set to ozone values at any value below 0.1 ppm.

The control panel 400 may be positioned on a top side 199 of the housing 100. The control panel is in electrical communication with the UV lamp 320 and the ozone lamp 340. In the embodiment shown, the UV lamp 320 and the ozone lamp 340 are directly connected or engaged to the control panel 400 through ports 410 in the top side 199 of the housing 100.

A flow sensor 370 is also in electrical communication with the control panel 400. The flow sensor 370 is positioned in the interior 120 of the housing. When the flow sensor 370 detects movement of air in the housing 100, the control panel 400 turns on both the ozone lamp 340 and the UV lamp 320. The control panel 400 may comprise a programmable logic controller such as a commercially available LCIC-1106A Loadcells interface card. The air decontamination unit 10 operates on standard alternating current. The control panel 400 includes a relay board 482, a multiplexer 484, a serial interface 486, and led lights 488 in electrical communication.

The control panel 400 comprises operating modes of low, medium, high and boost, which provide varying levels of ozone gas. The different operating modes increase the power supplied to the to the ozone lamp 340. The low ozone output level may be used in spaces of approximately 1500-2600 square feet. The medium ozone output level may be used in spaces of approximately 2600-3750 square feet. The high ozone output may be used in spaces of approximately 3750-4900 square feet. The boost ozone output level may be used in spaces of approximately 4900-6000 square feet.

The air decontamination unit 10 may be easily moved from location to location due to its compact size and wheels 130. In the alternative, the air decontamination unit 10 may be permanently or temporarily positioned in line with a conventional HVAC system that heats and cools a room or facility.

The blower 300 exhausts air comprising ozone gas at approximately 1000 cubic feet per minute to approximately 3000 cubic feet per minute. The control panel 400 may comprise different speeds for the blower 300, such as a high speed, which processes approximately 2600 cubic feet per minute and a low speed that process approximately 1300 cubic feet per minute. The operator may adjust the speed of the blower 300 by choosing the desired speed at the control panel 400. The exhaust port 195 funnels the air exhausting from the housing. The exhaust port 195 and blower 400 operate in conjunction to exhaust the cleaned and sanitized air.

Figure 4:
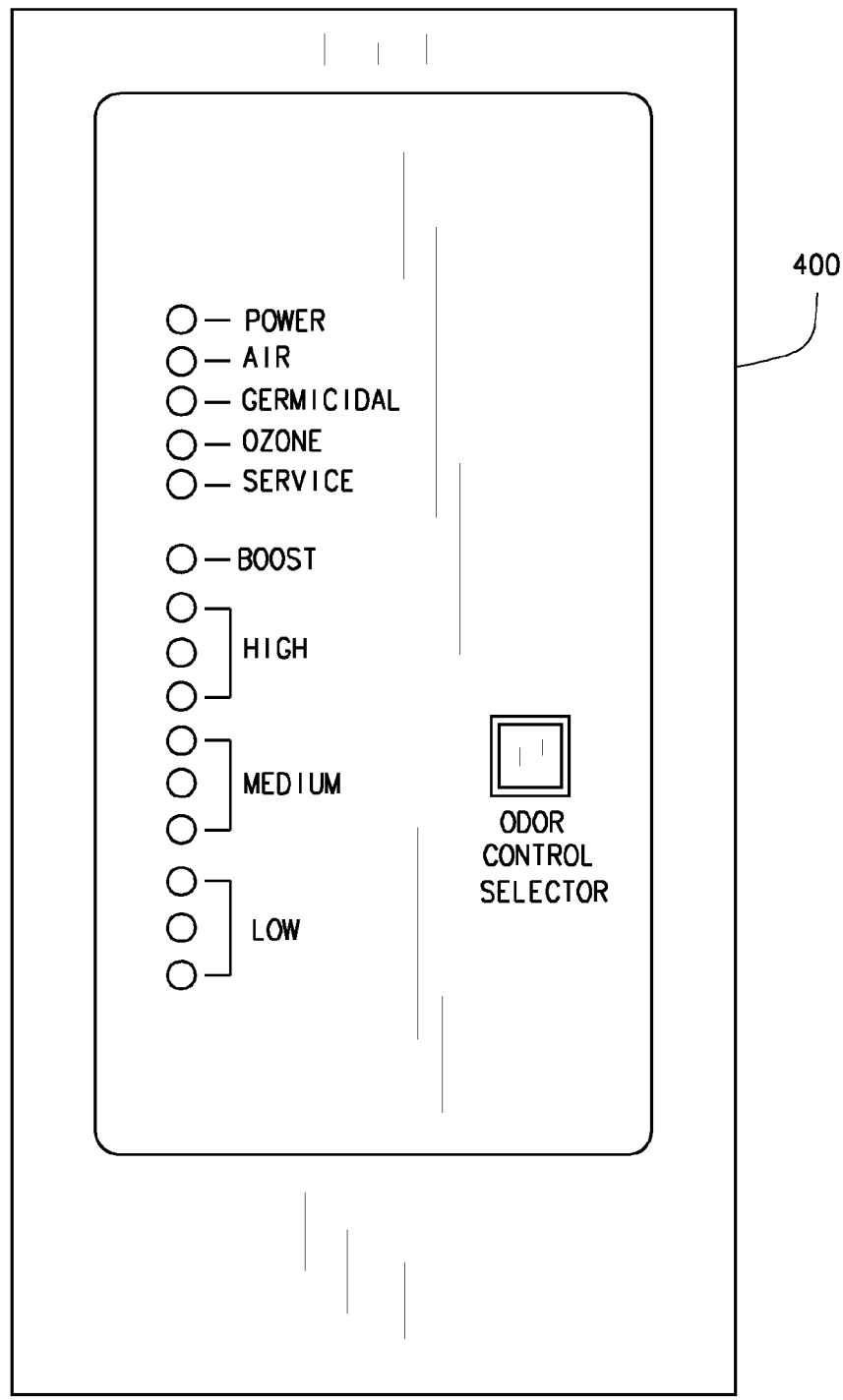
FIG. 4 is view of the status indicators on top of the control panel.

As shown in FIG. 4, the control panel 400 includes a visual output of LED signals showing the various modes and status of the control panel 400. For example, indicator lights are provided to show the status of power to the air decontamination unit 10, whether the blower 300, germicidal, and ozone functions are operational, whether service is required for the air decontamination unit 10, and whether the boost, high, medium, or low is the current status of the ozone lamp 340.

Figure 5:
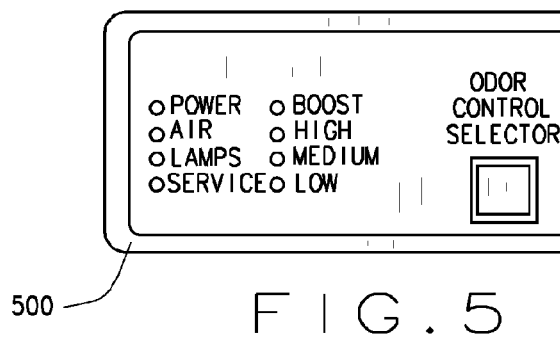
FIG. 5 is a view of the remote control.
Figure 6:
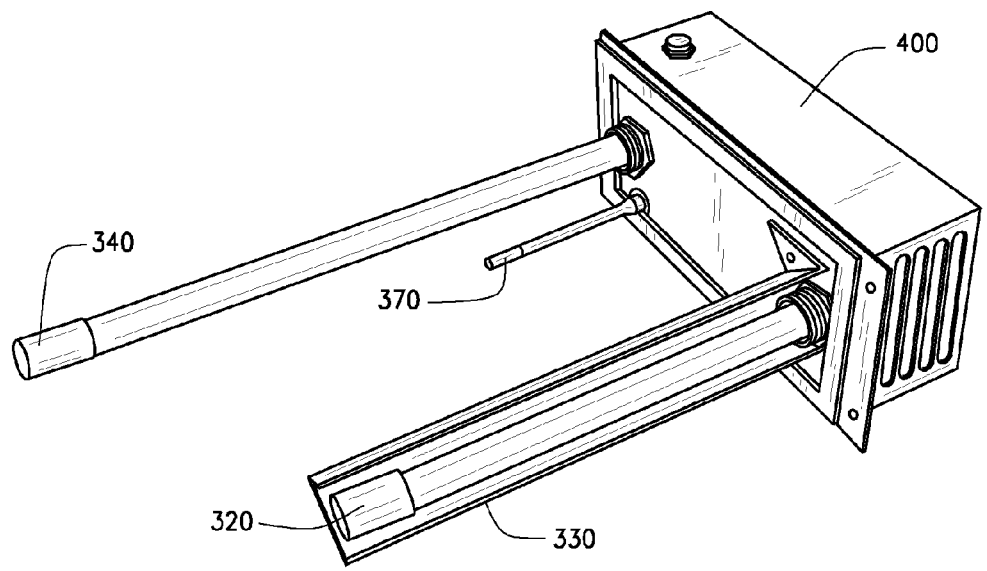
FIG. 6 is a perspective view of the control panel, the UV lamp, and the ozone lamp.
Figure 7:
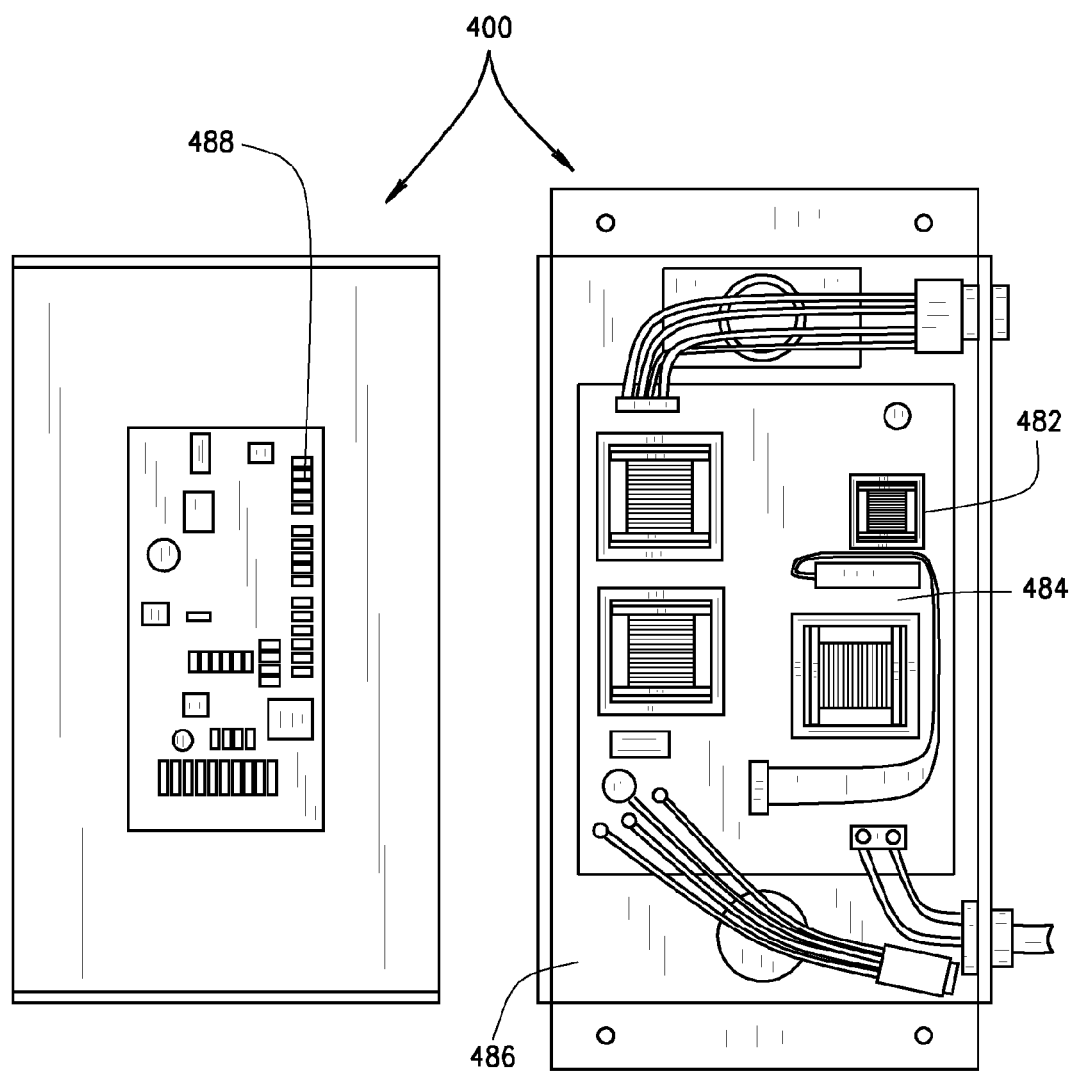
FIG. 7 is a view of the components and circuits of the control panel.

With reference to FIG. 5, an optional remote 500 is shown. The remote 500 generally includes the same status modes as the control panel 400. The remote 500 allows for the operator to remotely control the air decontamination unit 10.

The blower 300 is a commercially available unit from the Emerson Corporation. A blower 300 with a motor having approximately one horsepower to approximately two horsepower is suitable for the purposes described herein. A motor with a centrifugal style fan is suitable. The blower 300 pulls contaminated air through the clean filters at a static pressure of approximately 1.7 to approximately 2.0 inches of water column. One of ordinary skill in the art may increase or decrease the horsepower for larger or smaller applications.

The exhaust side 190 may include a number of controls and gauges for the air decontamination unit 10. A minihelic gauge 420 may be placed on the exhaust side wall 190. The minihelic gauge 420 is in operational communication with the interior of the air decontamination unit 10 to measure the pressure of the air in the air decontamination unit 10 to insure that the filter assembly 200 is not obstructed or blocked and is allowing air to enter and exhaust from the air decontamination unit 10. An on/off switch 440 is provided to turn the air decontamination unit 10 on and off. An hours monitor 450 may be provided to measure the usage of the air decontamination unit 10.

The air decontamination unit 10 provides a high velocity of cleaned and sanitized air into its ambient environment. The negative pressure created by the air decontamination unit intensifies the cleaning and sanitizing processes of the air decontamination unit. The high velocity of the exhaust air circulates about the room and expands into cracks and crevices where germs and other microbes and contaminants may be located. This high velocity of air is helpful in cleaning and sanitizing the various nooks and crannies in a particular room, such as in a keyboard, and other narrow or tight openings.

Ozone gas is generally unstable (a property that gives ozone its extraordinary oxidizing capabilities). Ozone gas cannot be packaged or stored and must be generated on site. Ozone creates none of the trihalomethanes commonly associated with chlorine compounds and properly matched to the application; ozone will reduce most organic compounds to carbon dioxide, water and a little heat. Finally, as ozone sheds the atom of the oxygen causing its molecular instability during the oxidation process, it becomes oxygen again. As such, an air decontamination unit 10 poses no health hazards. While ozone is a toxic gas and the established concentration limits must be adhered to, the odor threshold of 0.01 ppm is far below the safety limit of 0.1 ppm exposure over an eight hour period. The first symptoms of excessive ozone exposure are headaches, eye, nose or throat irritation or a shortness of breath. These symptoms can be relieved by the simple application of fresh air. While no deaths have been reported from ozone, sound safety practices deserve attention.

In the embodiment shown in the Figures, the air decontamination unit 10 has a size of approximately 33 inches long by 26 inches wide by 26 inches high and weighs approximately 145 pounds. These dimensions for the air decontamination unit 10 allow it to pass through a conventional 28-inch doorway. These dimensions allow the air decontamination unit 10 to be moved from room to room in order to clean and sanitized different spaces.

The air decontamination unit 10 may be utilized in medical facilities and food processing facilities. The air decontamination unit 10 reduces the level of microorganisms in these facilities resulting in reduce infections in the medical facilities and reduced spoilage in the food processing faculties.

The air decontamination unit 10 may be located within an isolation room in a medical facility with no inlet or exhaust ducting, so there is no affect on room pressurization. This setup accelerates the removal rate of airborne contaminants and provides supplemental ACH (air changes per hour) equivalents. The air decontamination unit 10 is user-friendly, functional and engineered to provide the highest level of micro-decontamination. The air decontamination unit 10 may be operated in a room or facility on a constant basis, i.e., 24 hours per day, seven days a week. The air decontamination unit 10 provides versatile, in-room operation providing outstanding short-term and long-term patient isolation solutions by meeting the Center for Disease Control's Guidelines for Infection Control in Healthcare Facilities using a range of negative or positive pressure modes of operation. The air decontamination unit 10 may be especially appropriate for facilities concerned about the possible need to add surge capacity in response to a bioterrorism event or a pandemic. The air decontamination unit 10 may be used in combination with the in-room HEPA filtration systems to help minimize any possibility that highly infectious biological pathogens can migrate into other areas of the facility.

Those skilled in the art will appreciate that variations from the specific embodiments disclosed above are contemplated by the invention. The invention should not be restricted to the above embodiments, but should be measured by the following claims.

What is claimed:

1. An air decontamination unit, comprising:
a housing defining an interior, the housing comprising an intake and an exhaust, the intake and exhaust in communication with the interior;
a blower for drawing air into the housing, moving air through the interior of the housing and exhausting the air;
a filter assembly for filtering air entering the housing through the intake;
a control panel in operational communication with the blower;
an ozone lamp positioned in the interior of the housing, the ozone lamp in electrical communication with the control panel;
a UV lamp positioned in the interior of the housing, the UV lamp in electrical communication with the control panel;
the control panel is positioned on a top side of the housing, and the UV lamp and the ozone lamp are directly connected or engaged to the control panel through ports in the top side of the housing; and,
an ozone sensor in electrical communication with the control panel for measuring the concentration of ozone gas in the interior of the housing.

2. The air decontamination unit according to claim 1, wherein the control panel comprises a mode for turning off the ozone lamp when the ozone sensor measures a concentration of greater than 0.1 parts per million of ozone gas.

3. The air decontamination unit according to claim 1, wherein the ozone lamp emits radiation at approximately 185 nanometers.

4. The air decontamination unit according to claim 1, wherein the UV lamp emits radiation at approximately 254 nanometers.

5. The air decontamination unit according to claim 1, wherein the filter assembly comprises a particulate filter, an anti-bacterial filter, and a 0.3 micron hepa filter.

6. The air decontamination unit according to claim 1, wherein the UV lamp is at least partially surrounded by a UV lamp trap.

7. The air decontamination unit according to claim 1, wherein UV lamp trap comprises an angled, rounded or semicircular plate or extension extending most of or the entire length of the UV lamp.

8. The air decontamination unit according to claim 7, wherein the UV lamp trap increases contact time between the UV lamp and air entering the housing.

9. The air decontamination unit according to claim 1, wherein a flow sensor is in electrical communication with the control panel, wherein the flow sensor monitors movement of air in the air decontamination unit and the control panel turns on the UV lamp and ozone lamp after the flow sensor detects the movement of air in the air decontamination unit.

10. The air decontamination unit according to claim 1, wherein the housing comprises casters or wheels, and the air decontamination unit may be rolled from one room to another.

11. The air decontamination unit according to claim 1, wherein the control panel comprises modes for operating the ozone lamp, wherein the modes comprise output levels of low, medium, high and boost.

12. The air decontamination unit according to claim 1, wherein the air entering the intake of the air decontamination unit first passes through the filter assembly, and then to the UV lamp, wherein the air next passes to the ozone lamp, wherein the air is exhausted from the housing by the blower.

13. The air decontamination unit according to claim 1 further comprising a remote control unit in operational communication with the control panel.

14. The air decontamination unit according to claim 1, wherein the control panel comprises a first mode for turning off the ozone lamp when the ozone sensor measures a concentration of greater than 0.1 parts per million of ozone gas and second mode for turning the ozone lamp back on after the ozone concentration has lowered to approximately 0.09 ppm.

15. The air decontamination unit according to claim 1, wherein the control panel monitors and operates the ozone lamp to maintain a constant ozone residue at approaching or approximately just under 0.1 ppm.

16. The air decontamination unit according to claim 1, wherein the air decontamination unit exhausts air comprising ozone gas at approximately 1000 cfm to approximately 3000 cfm.

17. An air decontamination unit, comprising:
a housing having side walls, a front wall, a rear wall, a bottom wall and a top wall, wherein the front wall comprises an exhaust port and the rear wall comprises an intake manifold;
the exhaust port and the intake manifold are in communication with an interior of the housing;
a blower for drawing air into the housing and moving air through the interior of the housing;
a control panel in operational communication with the blower;
the control panel positioned on a top wall of the housing;
an ozone lamp positioned in the interior of the housing, the ozone lamp in direct operative engagement with the control panel; and
a UV lamp positioned in the interior of the housing, the UV lamp in direct operative engagement with the control panel.

18. The air decontamination unit according to claim 17, wherein the UV lamp and the ozone lamp pass through ports in the top wall and into the interior of the housing.

19. An air decontamination unit, comprising:
a housing defining an interior, the housing comprising an intake and an exhaust, the intake and exhaust in communication with the interior;
a blower for drawing air into the housing and moving air through the interior of the housing;
a control panel in operational communication with the blower;
an ozone lamp positioned in the interior of the housing, the ozone lamp in electrical communication with the control panel;
a UV lamp positioned in the interior of the housing, the UV lamp in electrical communication with the control panel;
wherein a flow sensor is in electrical communication with the control panel, wherein the flow sensor monitors movement of air in the air decontamination unit and the control panel turns on the UV lamp and ozone lamp after the flow sensor detects the movement of air in the air decontamination unit;
an ozone sensor in electrical communication with the control panel for measuring the concentration of ozone gas in the interior of the housing; and wherein the control panel monitors and operates the ozone lamp to maintain a constant ozone residue at approaching or approximately just under 0.1 ppm.

20. The air decontamination unit according to claim 19, wherein the control panel comprises a first mode for turning off the ozone lamp when the ozone sensor measures a concentration of greater than 0.1 parts per million of ozone gas and second mode for turning the ozone lamp back on after the ozone concentration has lowered to a threshold lower than 0.1 ppm.

21. The air decontamination unit according to claim 20, wherein the threshold is approximately 0.09 ppm.

22. A method of sanitizing air, comprising:
    providing an air decontamination unit comprising: a housing defining an interior, the housing comprising an intake and an exhaust, the intake and exhaust in communication with the interior; a blower for drawing air into the housing and moving air through the interior of the housing; a filter assembly for filtering air entering the housing through the intake; a control panel in operational communication with the blower; an ozone lamp positioned in the interior of the housing, the ozone lamp in electrical communication with the control panel; a UV lamp positioned in the interior of the housing, the UV lamp in electrical communication with the control panel; the control panel is positioned on a top side of the housing, and the UV lamp and the ozone lamp are directly engaged to the control panel through ports in the top side of the housing; and an ozone sensor in electrical communication with the control panel for measuring the concentration of ozone gas in the interior of the housing;
    drawing air in to the air decontamination unit; and
    sanitizing the air in the air decontamination unit.

23. The method of sanitizing air according to claim 22, further comprising:
    providing the air decontamination unit in a first room or a first facility;
    operating the air decontamination unit in the first room or the first facility; and
    rolling the air decontamination unit to a second room or a second facility.

* * * * *